United States Patent [19]

Stout et al.

[11] Patent Number: 4,532,250
[45] Date of Patent: Jul. 30, 1985

[54] 5-HETEROARYLIMIDAZOL-2-ONES HAVING CARDIOTONIC ACTIVITY

[75] Inventors: David M. Stout, Vernon Hills; Diane M. Yamamoto, Gurnee, both of Ill.

[73] Assignee: American Hospital Supply Corporation, Evanston, Ill.

[21] Appl. No.: 554,498

[22] Filed: Nov. 23, 1983

[51] Int. Cl.³ ............................................. A61K 31/44
[52] U.S. Cl. .................... 514/341; 544/237; 544/284; 546/144; 546/167; 546/278; 548/127; 548/128; 548/134; 548/137; 548/317; 548/318; 548/322; 548/202; 548/206; 514/259; 514/248; 514/307; 514/311; 514/392
[58] Field of Search ......................... 546/278; 424/263

[56] References Cited

U.S. PATENT DOCUMENTS 3,538,104 11/1970 Gouenfeld et al. .................. 546/278
3,850,944 11/1974 Tanaka et al. ....................... 546/278

FOREIGN PATENT DOCUMENTS 59948   3/1982  European Pat. Off. .
78545  11/1982  European Pat. Off. .
78546  11/1982  European Pat. Off. .

OTHER PUBLICATIONS

Burger, Medicinal Chemistry, 2nd edition, 1960, p. 77.

Primary Examiner—Jane T. Fan
Attorney, Agent, or Firm—Gildo E. Fato

[57] ABSTRACT

Described are compounds of the formula

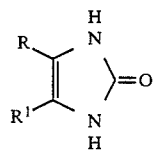

wherein R is heteroaryl and $R_1$ is hydrogen or loweralkyl, or a pharmaceutically acceptable salt thereof.

The compounds exhibit cardiotonic activity.

3 Claims, No Drawings

5-HETEROARYLIMIDAZOL-2-ONES HAVING CARDIOTONIC ACTIVITY

BACKGROUND OF THE INVENTION

Cardiotonic agents have been used for the treatment of heart failure for some time with digitalis continuing to be one of the principle pharmacologic agents used for this purpose, although the cardiac glycosides as a class do have some limitations. The output is regulated by the integration of the contractile state of the heart and the dynamics of the periphery circulatory system. When the heart fails, the primary problem is impairment of ventricular myocardial contractility which results in inadequate cardiac output to meet the metabolic and circulatory demands of the body. Effective therapy of heart failure is accomplished by either enhancing the contractile state of the heart with positive inotropic agents, or by adjusting the peripheral circulatory state with pheripheral vasodilators. Agents which stimulate myocardial contractility are of considerable value in the treatment of heart failure. Conventional therapy for heart failure has been the use of digitalis preparations which are the only orally effective inotropic drugs available for use in the treatment of this condition. However, their peripheral vascular effects are undesirable. Sympathomimetic amines are the other major class of cardiac stimulants which are used for the treatment of heart failure. The use of these agents is likewise limited, because they are not fully effective when administered orally and because of undesirable peripheral vasoconstrictor action. Currently, dobutamine and dopamine are the sympathomimetic agents which are primarily used for heart failure.

A promising inotropic agent which has been studied recently is the bipyridyl analog amrinone having the following formula:

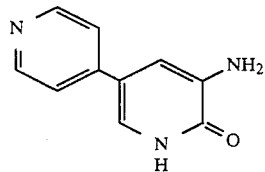

See Drug's of the Future, 4, 245 (1979), and A. E. Parah, et at, Life Sci., 22, 1139 (1978). In pentobarbital induced heart failure in dogs, amrinone caused an increase in both contractile force and cardiac output. However, experiments in dogs with experimentally induced ischemia indicate that amrinone and isoproterenol may increase acute ischemia and myocardial injury which could possibly limit the use of amrinone in heart failure patients with acute myocardial ischemia.

The compound of the following formula

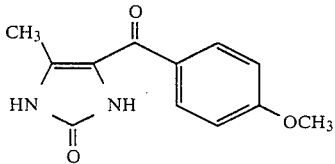

administered intravenously was found to increase myocardial contractile force and heart rate and decrease blood pressure in anesthetized dogs. The compound produced greater hemodynamic effects in dogs with experimentally induced heart failure that than in normal dogs, as reported by C. P. Hsieh, et al, Fed. Proc. Fed. Am. Soc. Exp. Biol., 39, 1106 (1980); and L. E. Roebel, et al, Pharmacologist, 22, 287 (1980).

SUMMARY OF THE INVENTION

The present invention is directed to compounds of the formula

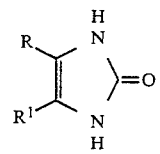

wherein R is heteroaryl and $R^1$ is hydrogen or loweralkyl, and pharmaceutically acceptable salts thereof.

The term "loweralkyl" as used herein refers to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "heteroaryl" includes bicyclic heteroaryl such as phthalazine, quinazoline, quinoline, or isoquinoline, and phenyl, either unsubstituted or substituted, naphthyl, thiazole, thiadiazole, thiophene, or pyridyl.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, and like salts. Also included are metallic salts such as the sodium or potassium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and, thus, includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For parenteral administration, amounts of from about 10 to 100 mg/kg per day per patient are useful, with the total dose of up to 0.2 to 2 grams per day being a suitable range for large animals, including humans. A preferred dosage range is from about 1 to 10 grams total daily dosage in a single or divided dose.

For all dosage forms the above exemplified compounds can be placed in capsules, formulated into pills, wafers, or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

The compounds of the invention can be made by the following described method, the reaction scheme illustrating a representative procedure.

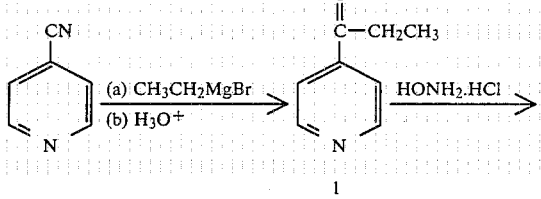

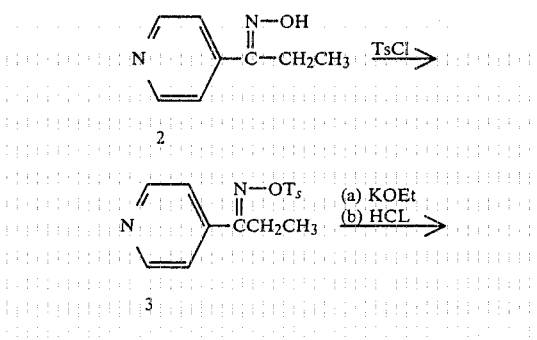

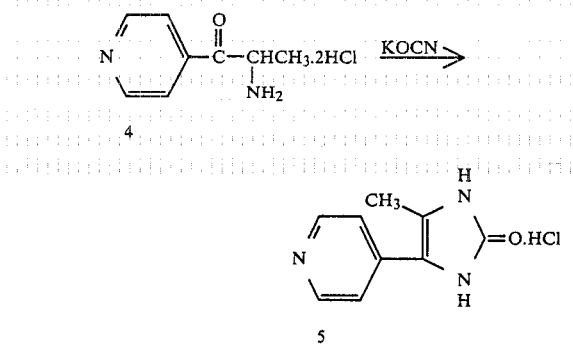

In order to illustrate the manner in which the above compounds may be prepared and the properties of the compounds, reference is made to the following examples, which, however, are not meant to limit or restrict the scope of the invention in any respect.

EXAMPLE 1

4-Propionylpyridine (1)

To a solution of 2.845M ethylmagnesium bromide (263 mL, 0.75 mol) in ethyl ether ($Et_2O$) (250 mL) was slowly added a solution of 4-cyanopyridine (39 g, 0.375 mol) in $Et_2O$ (750 mL). The reaction mixture was warmed at reflux for 12 hours, treated with concentrated $H_2SO_4$ (125 mL)/$H_2O$ (125 mL), and then washed three times with $Et_2O$ (250 mL). The aqueous portion was made basic (pH 9) with 15% NaOH solution and extracted five times with 250 mL portions of $Et_2O$. The combined $Et_2O$ extracts were dried ($MgSO_4$), and the solvent was removed under reduced pressure to afford a brown oil (48.4 g, 95%). Purification by vacuum distillation at 93°–97° (2.6 mm) afforded product as a pale yellow oil (25.35 g, 50%), NMR ($CDCl_3$) δ 1.23 (t, 3H, J=7 Hz), 3.00 (q, 2H, J=7 Hz), 7.70 (d, 2H, J=6 Hz), and 8.78 (d, 2H, J=6 Hz); IR (film) 1695 cm$^{-1}$.

EXAMPLE 2

4-Propionylpyridine oxime (2)

To a solution of hydroxylamine hydrochloride (7 g, 0.1 mol) in $H_2O$ (40 mL) and 2N NaOH solution (50 mL) was added the compound 1 (9.46 g, 70 mmol). The reaction mixture was heated to reflux and made homogeneous by the addition of methanol (MeOH) (30 mL). After heating at reflux for 2 hours, the reaction mixture upon cooling gave the compound 2 as a white solid (7.90 g, 75%): mp 141°–144° C.; NMR (DMSO-$d_6$) δ 1.03 (t, 3H, J=8 $H_z$), 2.72 (q, 2H, J=8 $H_z$), 3.34 (bs, 1H), 7.56 (d of d, 2H), and 8.56 (df d, 2H); IR (KBr) 1600 cm$^{-1}$.

EXAMPLE 3

4-Propionylpyridine oxime tosylate (3)

To the oxime 2 of Example 2 (5.0 g, 33 mmol) dissolved in pyridine (31 mL) was added p-toluenesulfonyl chloride (7.4 g, 39 mmol) and the reaction mixture stirred at room temperature for 24 hours. Pyridine hydrochloride was removed by filtration and the filtrate concentrated under reduced pressure. The solid obtained was slurried in hexanes, filtered, and air dried to give the compound 3 as a pale peach-colored solid: NMR ($CDCl_3$) δ 1.12 (t, 3H, J=8 $H_z$), 2.45 (s, 3H), 2.81 (q, 2H, J=8 $H_z$), and 7.27–7.98 (m, 8H).

EXAMPLE 4

4-(α-aminopropionyl)pyridined dihydrochloride (4)

To a solution of KOEt (2.4 g, 28.5 mmol) in absolute ethanol (EtOH) (25 mL) was added a solution of compound 3 (7.9 g, 26 mmol) dissolved in absolute EtOH (40 mL). After stirring at room temperature for 3.5 hours, the reaction mixture was treated with $Et_2O$ (400 mL) and filtered. The filtrate was extracted with several portions of 2N HCl and the aqueous extracts concentrated under reduced pressure to give a white solid which was washed with a small amount of cold MeOH and dried under vacuum to give the compound 4 as a white solid (2.64 g, 46%): NMR (DMSO-$d_6$) δ 1.39 (d, 3H, J=7 $H_z$), 5.13 (m, 1H), 8.15 (d, 2H), 8.52 (m, 1H), and 8.61 (d, 2H).

EXAMPLE 5

4-Methyl-5-(4 pyridyl)-2-imidazolone hydrochloride 5

To the compound 4, (1.115 g, 5 mmol) dissolved in water (5 mL) was added 6N HCl (0.85 mL, 5 mmol) and a solution of KOCN (0.81 g, 10 mmol) in water (5 mL). After refluxing for 2 hours, the product was removed by filtration and dried to give the compound 5 as a pale yellow solid (0.47 g, 40%): NMR (DCl) δ 2.55 (s, 3H), 8.02 (d, 2H, J=7 $H_z$), and 8.75 (d, 2H, J=7 $H_z$). Analysis calculated for $C_9H_9N_3O.HCl.1\frac{1}{3}H_2O$: C, 45,89; H, 5.17; N, 17.82. Found: C, 45.88; H, 5.42; N, 17.83

The described compounds are active inotropic or cardiotonic agents. They have been found to increase the contractile force of the heart while having minimal effects on blood pressure and heart rate and can be used in treating patients with diseased hearts for the purpose of increasing cardiac efficiency through a selective increase in the cardiac contractile force.

The cardiotonic activity of the compounds was established using the following test procedure:

Male Hartley strain guinea pigs (250–500 g body weight), obtained from Hilltop Lab Animals (Scottdale, PA), were stunned by a blow to the head and the left atria removed and rinsed in a modified Kreb's-Henseleit buffer. The buffer was continuously gassed with 95% oxygen and 5% carbon dioxide and was composed of the following: NaCl, 118 mM; KCl, 4.7 mM; $MgSO_4$, 1.2 mM; $KH_2PO_4$, 1.2 mM; $CaCl_2$, 1.25 mM; $NaHCO_3$, 25 mM; $Na_2EDTA$, 0.03 mM and D-glucose, 11 mM. The left atria were pierced through one end of the atrial appendage by a platinum hook connected to a fine gold chain and pierced at the other end of the appendage by a partially shielded platinum hook fixed to a glass rod.

The glass rod and atrium were suspended in a 30 ml water-jacketed tissue bath containing the Kreb's buffer at 33° C. Also connected to the glass rod was a second shielded platinum wire which was adjusted so that a 3–5 mm length of an unshielded portion of the wire was in contact with the atrium very near to the first shielded wire. Both platinum wires were connected to a Grass CCU1A constant current unit and a current was applied by a Grass S44 stimulator to drive the atrium by means of "point" stimulation. The parameters of stimulation were 1–3 mAmps, 1.5 Hz and 5 msec pulse duration. Each tissue was stretched to an initial resting tension of 1.0 g without further readjustment and washed periodically with fresh Kreb's buffer over a one-hour interval.

Developed tension was measured from a Statham UC-3 force transducer connected to the gold chain and recorded on a Gould 2800S recorder. The force signal was also passed to the A/D converter of a MINC-23 computer where the force signal was derivatized to calculate several characteristics of the contractile waveform.

After the one-hour equilibration period, test compounds were added cumulatively to the bath in small volumes (10–100 ul) at 10-minute intervals beginning at concentrations of $10^{-7}M$ and increasing by log or $\frac{1}{2}$ log units until a concentration of $3 \times 10^{-3}M$ was reached.

Using the described procedure, the change in tension in milligrams is measured. An increase in tension indicates a greater contractile force. The increase in tension produced by several representative compounds is recorded in the following table:

| | |
|---|---|
| ISPROTERENOL | >1500 mg, 0.4 uM dose |
| AMRINONE | >1000 mg, 5 m mol |
| COMPOUND OF EXAMPLE 5 | >1043 mg, 3 m mol |

What is claimed is:

1. A method of treating or relieving the symptoms associated with cardiac insufficiency in a patient by a selective increase in the cardiac contractile force comprising administering to a patient in need of such a treatment a therapeutically effective amount of a compound of the formula

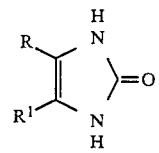

wherein R is pyridyl and $R_1$ is hydrogen or loweralkyl, or a pharmaceutically acceptable salt thereof.

2. The method of claim 1 where R is pyridyl and $R^1$ is loweralkyl.

3. The method of claim 2 wherein $R^1$ is methyl.

* * * * *